(12) United States Patent
Tyson, Jr.

(10) Patent No.: US 9,694,175 B2
(45) Date of Patent: Jul. 4, 2017

(54) TRANSVENOUS ACTIVE FIXATION LEAD SYSTEM

(75) Inventor: Archie A. Tyson, Jr., High Point, NC (US)

(73) Assignee: Medtronic, Inc., Minneapolis, MN (US)

( * ) Notice: Subject to any disclaimer, the term of this patent is extended or adjusted under 35 U.S.C. 154(b) by 1063 days.

(21) Appl. No.: 13/312,427

(22) Filed: Dec. 6, 2011

(65) Prior Publication Data

US 2012/0078266 A1 Mar. 29, 2012

Related U.S. Application Data

(62) Division of application No. 11/393,397, filed on Mar. 30, 2006, now Pat. No. 8,090,451.

(51) Int. Cl.
*A61N 1/00* (2006.01)
*A61B 19/00* (2006.01)
*A61N 1/05* (2006.01)

(52) U.S. Cl.
CPC ...... *A61N 1/057* (2013.01); *A61N 2001/0585* (2013.01)

(58) Field of Classification Search
CPC .................. A61N 1/057; A61N 2001/0585
USPC ......................................................... 607/122
See application file for complete search history.

(56) References Cited

U.S. PATENT DOCUMENTS

| | | | |
|---|---|---|---|
| 4,243,050 A | 1/1981 | Littleford | |
| 5,545,200 A | 8/1996 | West et al. | |
| 5,840,046 A | 11/1998 | Deem | |
| 5,964,795 A | 10/1999 | McVenes et al. | |
| 6,033,414 A * | 3/2000 | Tockman et al. | 606/129 |
| 6,132,390 A | 10/2000 | Cookston et al. | |
| 6,611,710 B2 | 8/2003 | Gomperz et al. | |
| 6,755,812 B2 | 6/2004 | Peterson et al. | |
| 6,836,687 B2 | 12/2004 | Kelley et al. | |
| 6,871,085 B2 | 3/2005 | Sommer | |
| 2002/0165537 A1 | 11/2002 | Kelley et al. | |
| 2003/0014099 A1 * | 1/2003 | Froberg et al. | 607/122 |
| 2003/0130598 A1 | 7/2003 | Manning et al. | |
| 2003/0144657 A1 | 7/2003 | Bowe et al. | |
| 2003/0208141 A1 | 11/2003 | Worley et al. | |
| 2003/0212446 A1 | 11/2003 | Kaplan et al. | |

(Continued)

FOREIGN PATENT DOCUMENTS

| | | |
|---|---|---|
| EP | 1 155 710 A1 | 11/2001 |
| WO | 0160447 A1 | 8/2001 |

(Continued)

OTHER PUBLICATIONS

Written Opinion of international application No. PCT/US2007/064280, dated Sep. 30, 2008, 6 pp.

*Primary Examiner* — Jason Flick
(74) *Attorney, Agent, or Firm* — Shumaker & Sieffert, P.A.

(57) ABSTRACT

A medical electrical lead system that includes a catheter extending from a proximal catheter end to a distal catheter end; a lead, insertable within the catheter, including a lead body extending from a proximal lead end to a distal lead end and an active fixation member positioned at the distal lead end; and an advancement tool for advancing the distal lead end outward from the distal catheter end. The advancement tool is adapted to be positioned around the lead body and further adapted to be removably fixedly engaged with the proximal catheter end.

15 Claims, 9 Drawing Sheets

(56) References Cited

U.S. PATENT DOCUMENTS

| | | |
|---|---|---|
| 2004/0019359 A1 | 1/2004 | Worley et al. |
| 2004/0064172 A1 | 4/2004 | McVenes et al. |
| 2004/0172116 A1* | 9/2004 | Seifert et al. ................. 607/119 |
| 2004/0215139 A1 | 10/2004 | Cohen |
| 2005/0020914 A1 | 1/2005 | Amundson et al. |
| 2005/0085886 A1* | 4/2005 | Hess et al. ................... 607/127 |
| 2007/0239241 A1 | 10/2007 | Tyson, Jr. |

FOREIGN PATENT DOCUMENTS

| | | |
|---|---|---|
| WO | 2005007228 A1 | 1/2005 |
| WO | 2005037368 A1 | 4/2005 |

* cited by examiner

Fig. 13

TRANSVENOUS ACTIVE FIXATION LEAD SYSTEM

This application is a divisional of U.S. patent application Ser. No. 11/393,397, filed Mar. 30, 2006, and issued as U.S. Pat. No. 8,090,451 the entire content of which is incorporated herein by reference.

TECHNICAL FIELD

The invention relates generally to implantable medical devices and, in particular, to an active fixation, transvenous lead and associated delivery system.

BACKGROUND

Transvenous endocardial leads may be placed inside a chamber of a patient's heart by passing the lead through a venous entry site, such as the subclavian vein or the cephalic vein, or a tributary thereof, along a venous pathway into the superior vena cava and into the right cardiac chambers. Cardiac vein leads may be advanced further, from the right atrium through the coronary sinus ostium into the coronary sinus and ultimately into one of the various cardiac veins for stimulation and/or sensing of the left heart chambers.

Cardiac lead placement is important in achieving accurate sensing of cardiac signals and proper cardiac stimulation pulse delivery for providing optimal therapeutic benefit from cardiac stimulation therapies such as cardiac resynchronization therapy (CRT). Cardiac vein leads generally need to be small in diameter to allow advancement through the cardiac veins and highly flexible in order to withstand flexing motion caused by the beating heart without fracturing. The small diameter and flexibility of the lead, however, makes advancement of the lead along a tortuous venous pathway challenging. Cardiac vein leads are generally implanted with the aid of a relatively stiff guide catheter and/or guidewire or stylet. Considerable skill and time are required to achieve proper placement of a transvenous lead along a cardiac vein site.

Cardiac vein leads have typically been provided with a passive fixation member and an atraumatic tip electrode. The passive fixation member provides fixation of the distal lead tip by becoming lodged within a narrow cardiac vein. The distal lead tip needs to be advanced into a cardiac vein that is small enough to securely lodge the lead tip therein. Dislodgement of a passively fixed cardiac vein lead can still occur, however, even when the lead tip is advanced into a small vein.

The requirement of advancing the lead into a narrow cardiac vein branch for fixation purposes imposes limitations on the possible implant locations that may be selected. An implant site in a larger vein may result in more optimal sensing or stimulation in a particular individual. Furthermore, advancement of leads deep into a small cardiac vein on the lateral free wall of the left ventricle can introduce undesired stimulation of the diaphragm during cardiac pacing.

BRIEF DESCRIPTION OF THE DRAWINGS

Aspects and features of the present invention will be appreciated as the same becomes better understood by reference to the following detailed description of the embodiments of the invention when considered in connection with the accompanying drawings, wherein.

DETAILED DESCRIPTION

In the following description, references are made to illustrative embodiments for carrying out the invention. It is understood that other embodiments may be utilized without departing from the scope of the invention. For purposes of clarity, the same reference numbers are used in the drawings to identify similar elements. Unless otherwise noted, drawing elements are not drawn to scale.

Figure 1:
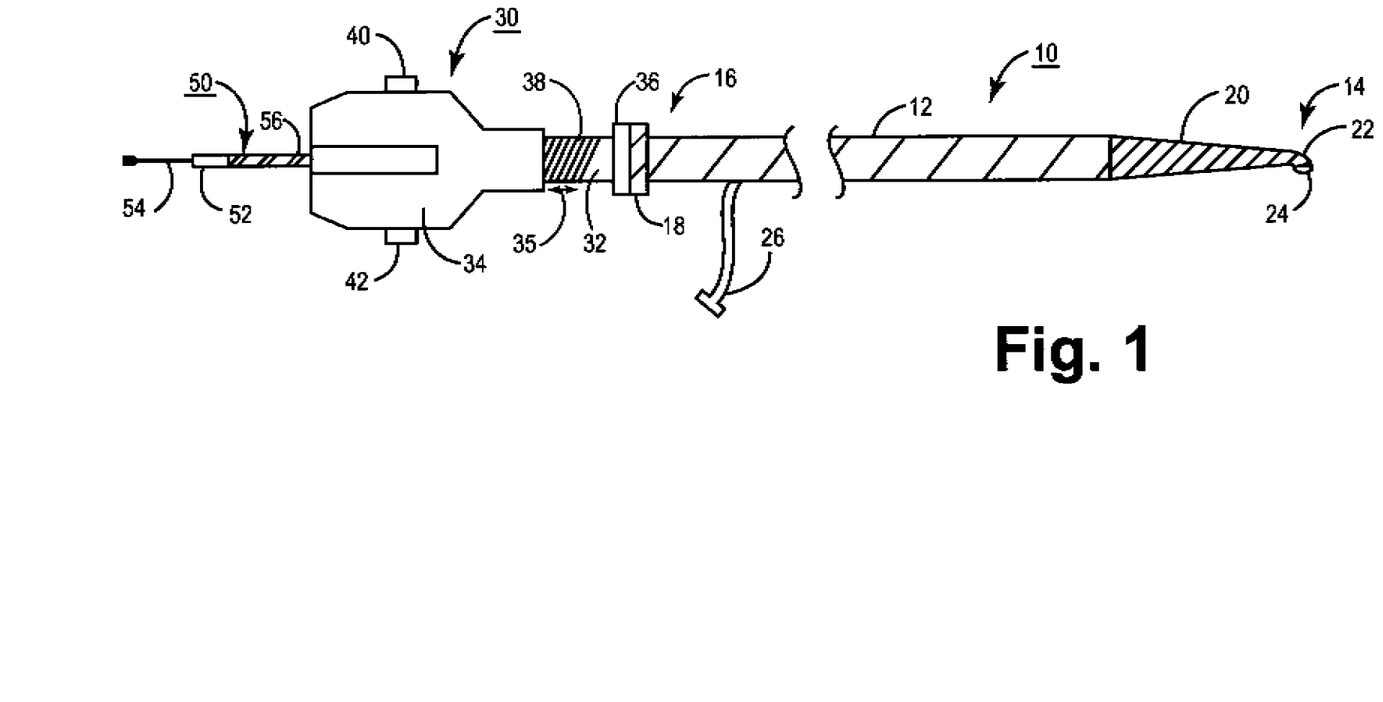
FIG. 1 is a plan view of transvenous lead and delivery system according to one embodiment of the invention.

FIG. 1 is a plan view of transvenous lead and delivery system according to one embodiment of the invention. The system includes a catheter 10, an advancement tool 30, a transvenous lead 50, and a guidewire 54. Catheter 10 includes tubular elongated body 12 extending between a distal catheter end 14 and a proximal catheter end 16. A working port 24 is provided at distal catheter end 14 through which guidewire 54, lead 50, or other instruments or devices may be advanced outward from distal catheter end 14. Proximal catheter end 16 is provided with a fitting 18 for removably fixedly engaging advancement tool 30. An injection port 26 may be provided to enable administration of contrast agents, dyes, or other fluids through catheter 10.

Elongated catheter body 12 includes a flexible distal portion 20 having greater flexibility than the remainder of catheter body 12. In one embodiment, flexible distal portion 20 is tapered toward proximate distal catheter end 14. Flexible distal portion 20 includes a distal curve or bend 22 for directing working port 24 radially outward, at any predetermined angle, from the central axis of catheter 10. Lead 50 (or another instrument) advanced outward from working port 24 will be directed in a radial direction away from the central axis of catheter 10. When catheter 10 is advanced into a cardiac vein and lead 50 is advanced outward from working port 24, lead 50 will be directed toward the vein wall rather than along the vein lumen.

Catheter 10 may be used as a subselection catheter that is advanced through a larger, generally stiffer, guide catheter. During one implant procedure for placing lead 50 in a cardiac vein location, a guide catheter is advanced into the right atrium and the coronary sinus. Catheter 10, having lead 50 and guidewire 54 retracted therein, is advanced through the guide catheter into the coronary sinus and further advanced to a cardiac vein branch. Guidewire 54 is advanced out of working port 24 into the desired cardiac vein branch. Catheter 10 is advanced over guidewire 54, into the selected cardiac vein and to a targeted implant site. The flexible distal portion 20 will track guidewire 54 along a tortuous pathway to the implant site. Guidewire 54 will act to straighten bend 22 such that distal catheter end 14 tracks guidewire 54 along the desired venous path. Guidewire 54 may be provided with a hydrophilic coating to allow lead 50 to glide easily over guidewire 54 with minimal resistance or friction. A hydrophilic coating may correspond to a polysaccharide coating as generally descried in U.S. Pat. No. 5,840,046 (Deem), hereby incorporated herein by reference in its entirety.

Verification of the position of working port 24 at the targeted implant site may be made by injection of a contrast agent through injection port 26. When the working port 24 of catheter 10 is positioned at the targeted implant site, guidewire 54 is removed. Advancement tool 30 is used to advance lead 50 outward from working port 24 to fixate the distal lead end at the implant site, as will be described in greater detail herein.

Advancement tool 30 includes a movable member 34 and a fixable member 32. Fixable member 32 is provided with a fitting 36 adapted for fixedly engaging catheter fitting 18 in a removable manner. For example, advancement tool fitting 36 and catheter fitting 18 may correspond to Luer lock fittings which mate to prevent lateral or passive rotational movement of fixable member 32 relative to catheter 10.

Movable member 34 is adapted to move laterally with respect to fixable member 32. In one embodiment, movable member 34 moves laterally with respect to fixable member upon rotation of movable member 34. Fixable member 32 includes screw-like threads 38 which mate with threads or a thread guide included in movable member 34. Movable member 34 moves laterally along fixable member 32, as indicated by arrow 35, upon rotation of movable member 34.

Movable member 34 is adapted to interface with the elongated body 56 of lead 50 to temporarily fix the position of lead 50 relative to movable member 34. In one embodiment, movable member 34 is provided with one or more lead engaging members embodies as set screws 40 and 42 which are tightened down to removably, fixedly engage lead 50, extending within a lumen of movable member 34. In alternative embodiments, clips, springs, hinged members or other lead engaging members may be included for fixedly engaging lead 50 in a removable manner. Upon rotation of movable member 34, lead 50 will move laterally with movable member 34 with respect to fixable member 32 and catheter 10.

Figure 2:
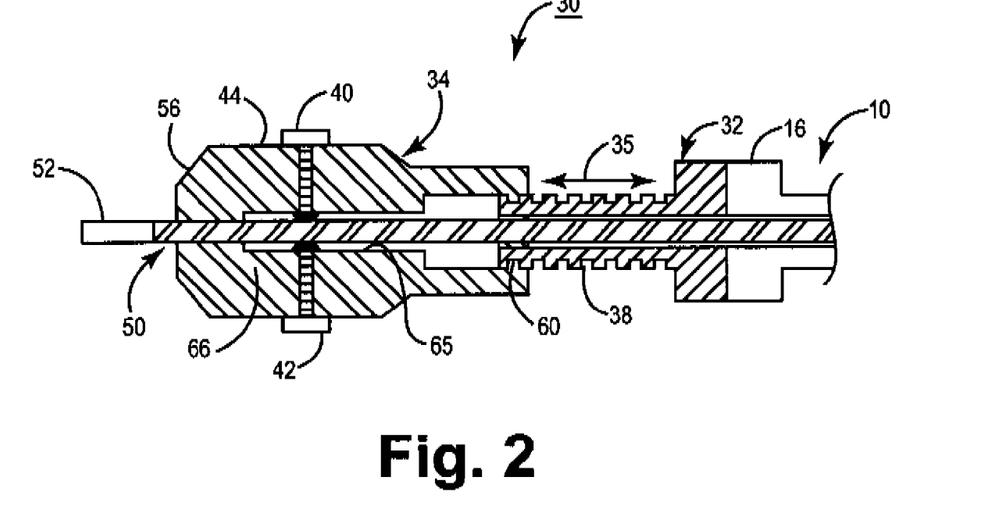
FIG. 2 is a sectional view of an advancement tool included in the delivery system of FIG. 1.

FIG. 2 is a sectional view of advancement tool 30. Advancement tool 30 includes an inner surface 65 forming central lumen 66 for receiving lead 50. Lumen 66 extends continuously through movable member 34 and fixable member 32. Lead 50 is stabilized within lumen 66 by set screws 40 and 42. Set screws 40 and 42 may be tightened down onto the elongated body 56 of lead 50. Alternatively, lumen 66 is provided with a deformable wall 44 that becomes pressed against lead body 56 when set screws 40 and 42 are tightened down toward lumen 66. Deformable wall 44 acts to protect the lead body from being damaged by set screws 40 and 42. Deformable wall 44 is formed of a material, such as silicone rubber, that forms a non-slip or slip resistant interface with lead body 56, which is typically formed of polyurethane.

In one embodiment, movable member 34 is provided with a thread guide 60 adapted to mate with threaded portion 38 of fixable member 32. As movable member 34 is rotated, thread guide 60 follows threaded portion 38 of fixable member 32 causing lateral movement of movable member 34 with respect to fixable member 32 as indicated by arrow 35. Lead 50 will be rotated and advanced through catheter 10 as movable member 34 is rotated in a first direction, typically a clockwise direction, with respect to fixable member 32. As will be described in greater detail herein, rotation of movable member 34 causes an active fixation member provided at the distal end of lead 50 to be advanced outward from the distal working port of catheter 10 and become fixedly engaged with adjacent tissue at the implant site. Lead 50 may be retracted by rotating movable member 34 in an opposite, typically counter-clockwise, direction.

Figure 3:
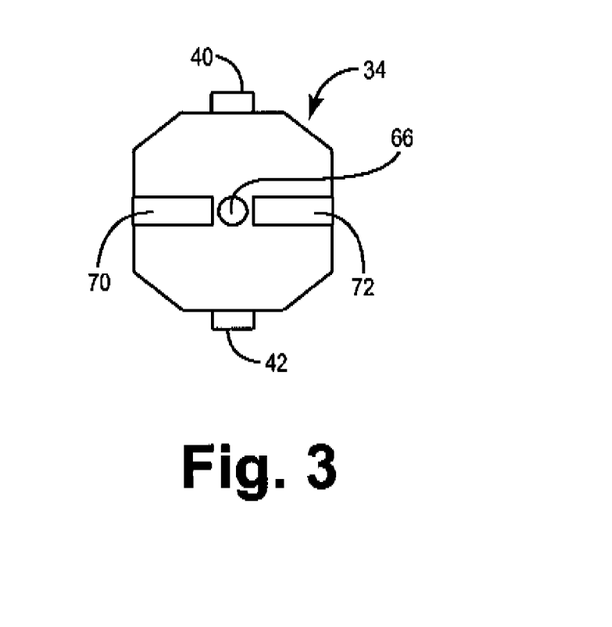
FIG. 3 is a proximal end view of a movable member included in the advancement tool of FIG. 2.

FIG. 3 is a proximal end view of movable member 34 included in advancement tool 30. Movable member 34 is provided with a cross-sectional size and shape that allows an implanting clinician to readily grip and rotate movable member 34 to facilitate advancement of a lead 50 extending through advancement tool lumen 66. In the example shown in FIG. 3, movable member 34 is provided with a generally octagonal shape however movable member 34 may be provided with other cross-sectional geometries, such as generally round, square or another polygonal shape. In some embodiments, movable member 34 may be provided with ridges or other non-slip features along its exterior surface to allow the clinician to easily grip movable member 34 without slippage. Lead engaging members embodied as set screws 40 and 42 are used to temporarily fix the position of a lead extending through lumen 66 relative to movable member 34. Movable member 34 includes one or more grooves 70 and 72 adapted for receiving flanges included on a torque transfer member as will be described below.

Figure 4:
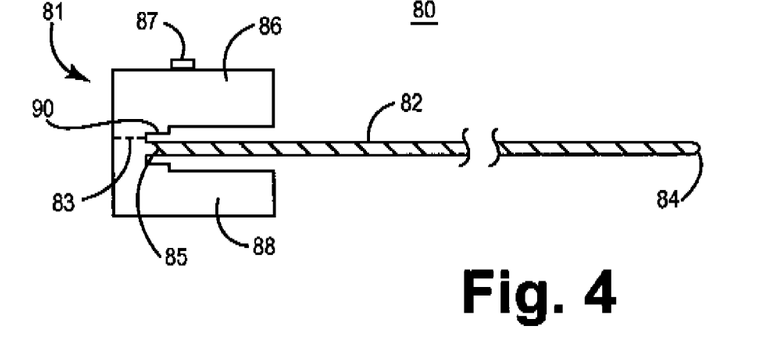
FIG. 4 is a plan view of one embodiment of a torque transfer member that may be included in the transvenous lead delivery system shown in FIG. 1.

FIG. 4 is a plan view of one embodiment of a torque transfer member that may be included in the transvenous lead delivery system shown in FIG. 1. Torque transfer member 80 includes a stylet 82 extending from a flanged handle 81. Stylet 82 extends between a distal end 84 and a proximal end 85 connected to handle 81. Handle 81 is designed to interlock with movable member 34 (shown in FIG. 3) In one embodiment, handle 81 is provided with one or more flanges 86 and 88 which interlock with a corresponding number of grooves 70 and 72 provided in movable member 34 (FIG. 3). It is recognized that numerous configurations are possible for providing interlocking members on handle 81 and movable member 34, which may include flanges, pegs, rods, grooves, notches, bores, or any other paired interlocking structures.

Handle 81 includes a lead engaging member embodied as a set screw 87 for securing the position of a proximal lead connector assembly between flanges 86 and 88. Handle 81 further includes a receptacle 90 for receiving and retaining the tip of a proximal lead connector pin. Receptacle 90 is sized to receive the proximal lead connector pin in a snap fit. Handle 81 may be provided as a splittable member having a perforation 83 to allow easy removal of torque transfer member 80 from a lead.

Figure 5:
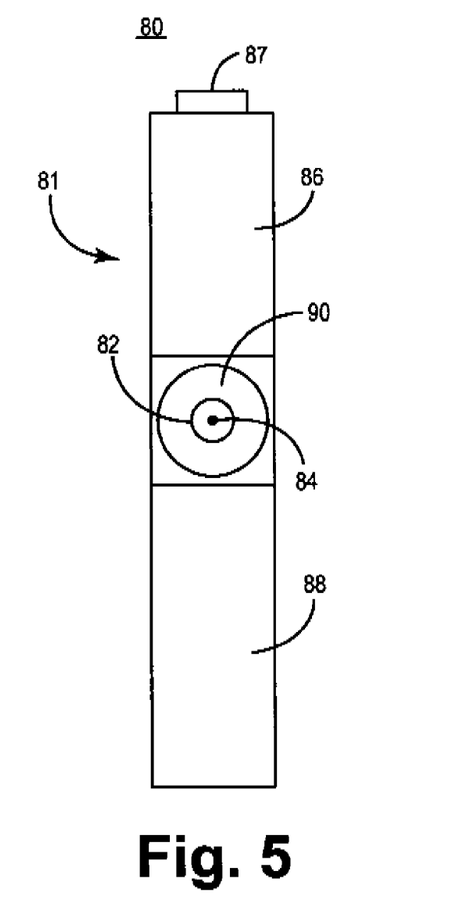
FIG. 5 is a distal end view of the torque transfer member shown in FIG. 4.

FIG. 5 is a distal end view of the torque transfer member 80 shown in FIG. 4. Flanges 86 and 88 extend radially from handle 81 and are provided with an outer dimension adapted for insertion in grooves 70 and 72 of movable member 34 (FIG. 3). Stylet 82 is advanced through a lead body until a proximal lead connector pin is securely positioned in receptacle 90.

Figure 6:
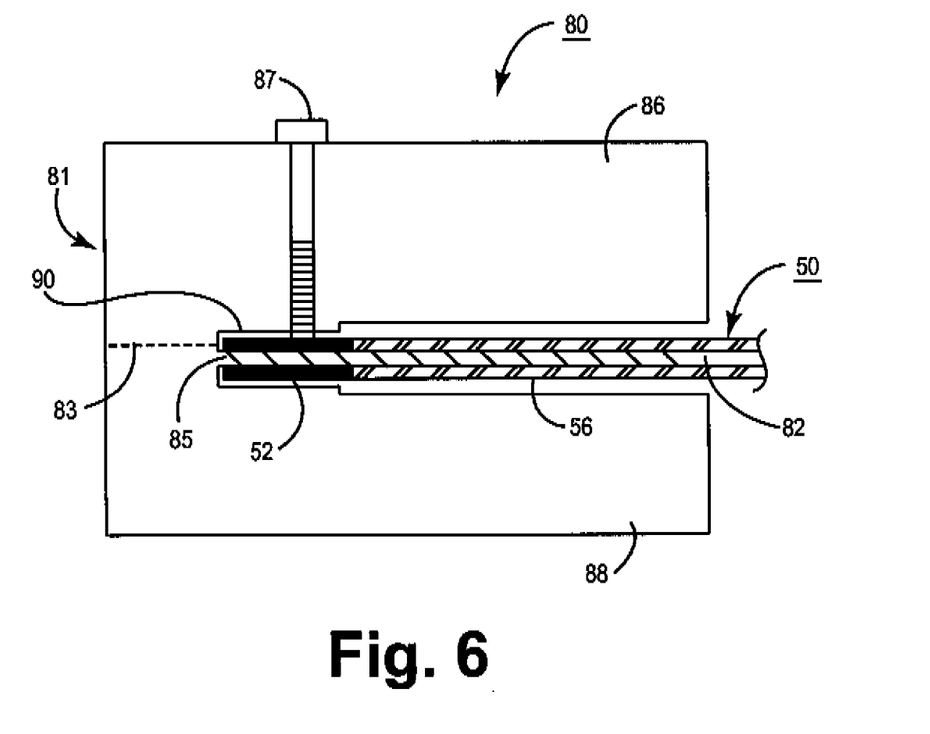
FIG. 6 is a plan view of the torque transfer member of FIG. 4 after advancing the stylet through a lead body.

FIG. 6 is a plan view of torque transfer member 80 after advancing stylet 82 through a lead body 56. Lead 50 includes a proximal connector pin 52 and an open lumen extending through lead body 56 adapted for receiving a guidewire or stylet. Stylet 82 is advanced through lead body 56 until proximal lead connector pin 52 reaches stylet proximal end 85 and is received by (snapped into) receptacle 90. Stylet 82 may be provided with a hydrophilic coating to reduce friction between lead body 56 and stylet 82 and thereby promote smooth advancement of stylet 82 through lead 50. Set screw 87 is tightened down on lead connector pin 52 to temporarily fix stylet 82 within lead 50 in a stable manner Receptacle 90 is sized to securely retain proximal lead connector pin 52.

Figure 7:
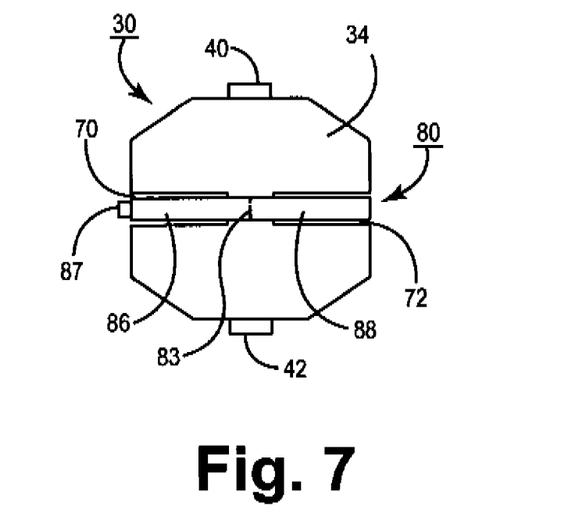
FIG. 7 is a proximal end view of the movable member of the advancement tool of FIG. 3 assembled with the torque transfer member of FIG. 4.

FIG. 7 is a proximal end view of movable member 34 assembled with torque transfer member 80. Lead 50 is advanced through advancement tool lumen 66 as shown in FIG. 2, and stylet 82 is advanced through lead 50 as shown in FIG. 6. Handle flanges 86 and 88 of torque transfer member 80 are inserted into movable member grooves 70 and 72 as shown in FIG. 7. Movable member set screws 40 and 42 and torque transfer member set screw 87 provide three torque transfer contact points with the lead positioned within advancement tool 30 and torque transfer member 80. An additional torque transfer contact point may be provided by including a fourth set screw in flange 88 of torque transfer member 80. Each lead engaging member, including set screws 40, 42, and 87 and proximal lead connector pin receptacle 90 (shown in FIG. 6), provides a contact point for transferring torque that is applied to rotate lead 50 during rotation of movable member 34.

Figure 8:
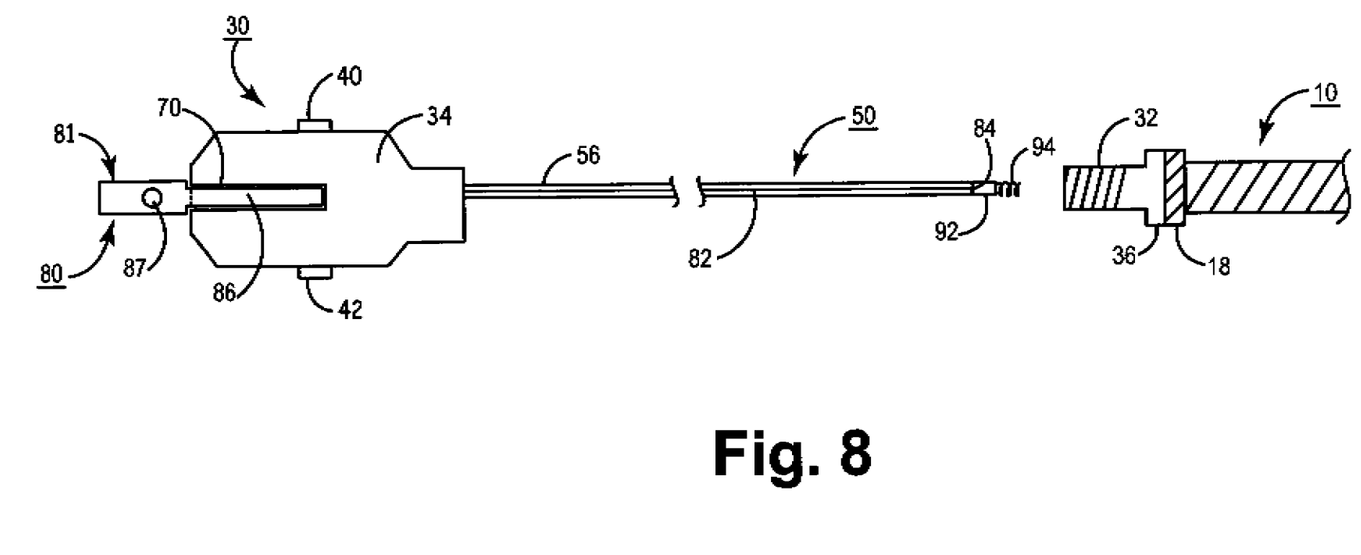
FIG. 8 is a plan view of a transvenous lead assembled with a torque transfer member and a movable member of an advancement tool.

FIG. 8 is a plan view of a transvenous lead assembled with torque transfer member 80 and movable member 34 of advancement tool 30. Stylet 82 is shown advanced through lead 50. Stylet 82 is provided with a length somewhat shorter than the length of lead body 56 such that stylet distal end 84 terminates proximal to lead distal end 92. The proximal lead connector pin is removably fixedly engaged by handle 80 as described above and shown in FIG. 6. Handle flange 86 is interlocked with movable member groove 70. Likewise, handle flange 88 is interlocked with movable member groove 72 (not visible in the view shown in FIG. 8). Set screws 40, 42, and 87 secure the position of lead 50 with respect to movable member 34 and torque transfer member 80. Lead 50 may be packaged pre-assembled with torque transfer member 80 and/or movable member 34. Lead 50 is advanced through fixable member 32 and catheter 10. Rotation of movable member 34 causes lateral motion of lead 50 which advances lead distal end 92 out the distal working port of catheter 10. As lead 50 is advanced, active fixation member 94 provided at lead distal end 92 is advanced into the tissue at a targeted implant site.

Figure 9:
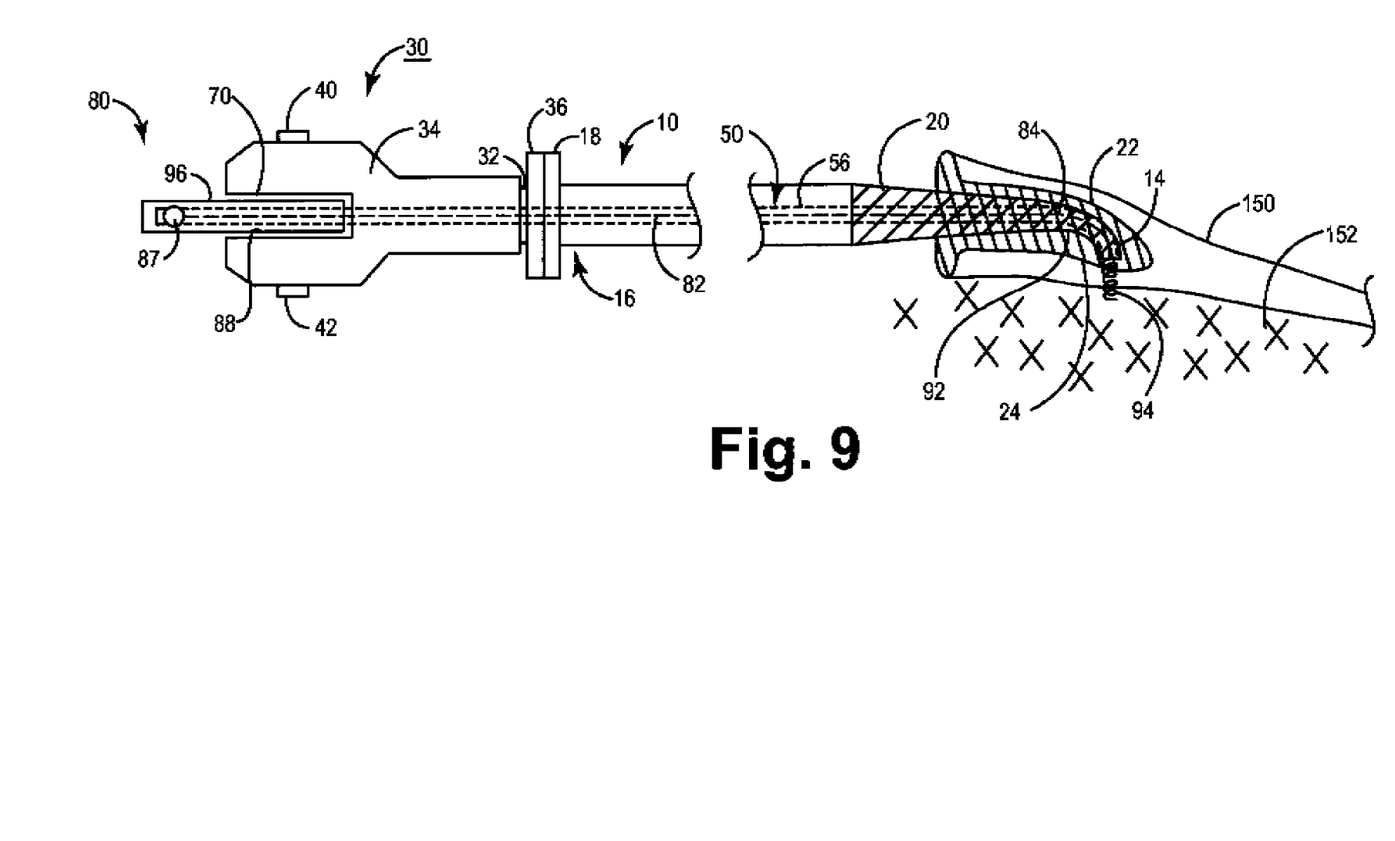
FIG. 9 is a plan view of a transvenous lead advanced through a catheter to a cardiac vein implant site.

FIG. 9 is a plan view of lead 50 advanced through catheter 10 to a cardiac vein implant site. During an implant procedure, catheter 10 is advanced over a guidewire 54 (shown in FIG. 1) into a selected cardiac vein as described previously. Catheter 10, advancement tool 30, lead 50 and guidewire 54 may be packaged preassembled and advanced as a single unit through a guide catheter into the coronary sinus. Lead 50 would remain retracted within catheter 10 during advancement of catheter 10 to a targeted implant site. Guidewire 54 would be used to subselect a desired cardiac vein branch, and catheter 10 would track guidewire 54 to a targeted implant site. Guidewire 54 would be removed from lead 50 when the targeted site is reached. Stylet 82 would then be advanced through lead 50 and torque transfer member handle 81 would be interlocked with advancement tool 30. Movable member 34 would then be rotated to advance active fixation member 94 out catheter working port 24 into tissue at the implant site. Movable member 34 is shown fully advanced onto fixable member 32, thereby extending distal fixation member 94 a controlled distance outward from working port 24.

Multiple torque transfer contact points provided by set screws 40, 42 and 87, and lead pin connector receptacle 90 within handle 81 (shown in FIG. 6) promote efficient torque transfer from movable member 34 to lead 50. Stylet 82 extending through lead body 56 adds torsional stiffness to lead body 56 and thereby promotes efficient torque transfer from the multiple torque transfer contact points along the proximal lead end to the distal lead end 92.

Stylet distal end 84 terminates proximal to distal lead end 92 and catheter bend 22. Fixation member 94 is directed radially outward through working port 94, away from the central axis of catheter 10 and the central lumen of cardiac vein 150. Fixation member 94 is directed into the wall of cardiac vein 150, in the direction of the underlying epicardial tissue 152. Distal lead end 92 can be reliably fixed in the tissue at a targeted implant site, even within a relatively large cardiac vein branch 150.

Figure 10:
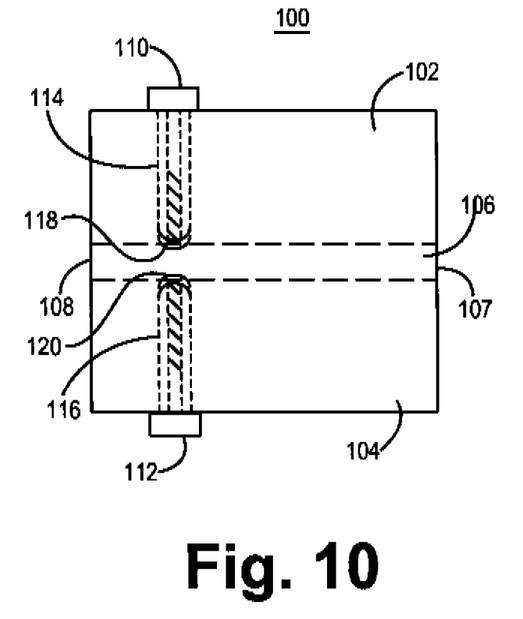
FIG. 10 is a plan view of an alternative embodiment of a torque transfer member.

FIG. 10 is a plan view of an alternative embodiment of a torque transfer member. Torque transfer member 100 includes one or more flanges 102 and 104 for interlocking with movable member 34 in the same manner as described above. Torque transfer member 100 includes a central lumen 106 extending between a proximal port 108 and a distal port 107 adapted for receiving a lead body extending through lumen 106. Torque transfer member 100 includes one or more bores 114 and 116 for receiving respective set screws 110 and 112. The base 118 of set screw bore 114 and the base 120 of set screw bore 116 are formed from a deformable material that allows set screws 110 and 112 to be advanced securely down onto a lead body extending through lumen 106 without causing damage to the lead body insulation. Set screw bore bases 118 and 120 are formed of a material such as silicone rubber that provides a non-slip or slip resistant coupling with the lead body insulation, typically formed of polyurethane. It is recognized that other lead engaging members may be used that allow fixation of a lead within torque transfer member 100 in a removable manner, such as clips, spring elements, hinged elements, collars, or other lead engaging members.

Figure 11:
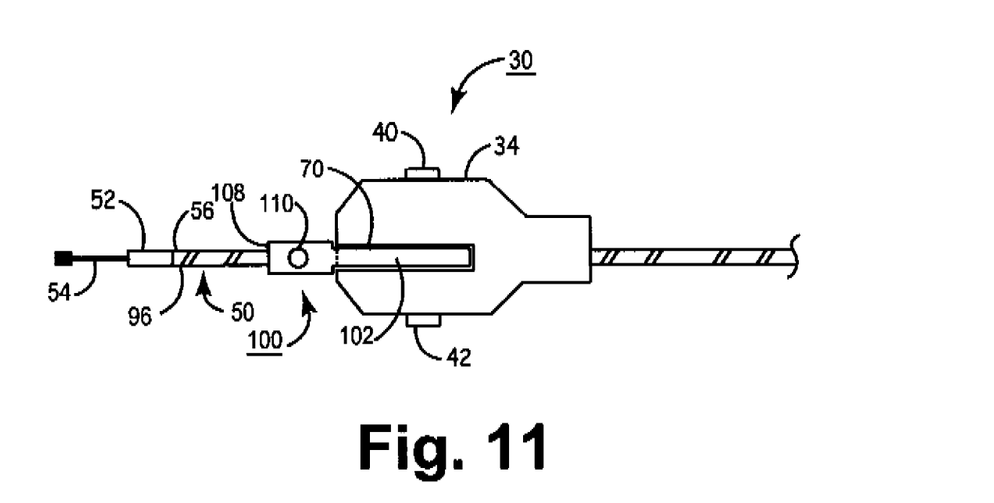
FIG. 11 is a plan view of the torque transfer member shown in FIG. 10 assembled with a lead and an advancement tool movable member.

FIG. 11 is a plan view of the torque transfer member 100 shown in FIG. 10 assembled with a lead 50 and advancement tool movable member 34. Lead body 56 extends through torque transfer member 100 and movable member 34. Torque transfer member flange 102 is interlocked with movable member groove 70. Likewise, flange 104 is interlocked with movable member groove 72 (not visible in the view shown in FIG. 11). Set screws 40, 42, 110 and 112 (shown in FIG. 10) removably, fixedly engage lead body 56 with torque transfer member 100 and movable member 34 and provide torque transfer contact points for causing rotation of lead 50 during rotation of movable member 34. The lead proximal end 96 extends outward from proximal port 108 of torque transfer member 100. A guidewire 54 may optionally extend through lead 50 to provide additional support to lead 50 during an implant procedure, for guiding lead 50 to an implant site and for adding torsional resistance during lead rotation.

Torque transfer member 100 having open proximal port 108 allows repositioning of lead 50 within torque transfer member 100 and movable member 34 during an implant procedure. Set screws 40, 42, 110 and 112 (shown in FIG. 10) may be loosened to allow torque transfer member 100 and movable member 34 to be moved along lead body 56. Repositioning of torque transfer member 100 and movable member 34 along lead body 56 may be needed during an implant procedure in order to advance the distal end of lead 50 a required distance outward from the working port of catheter 10 to achieve fixation at a desired implant site.

Figure 12:
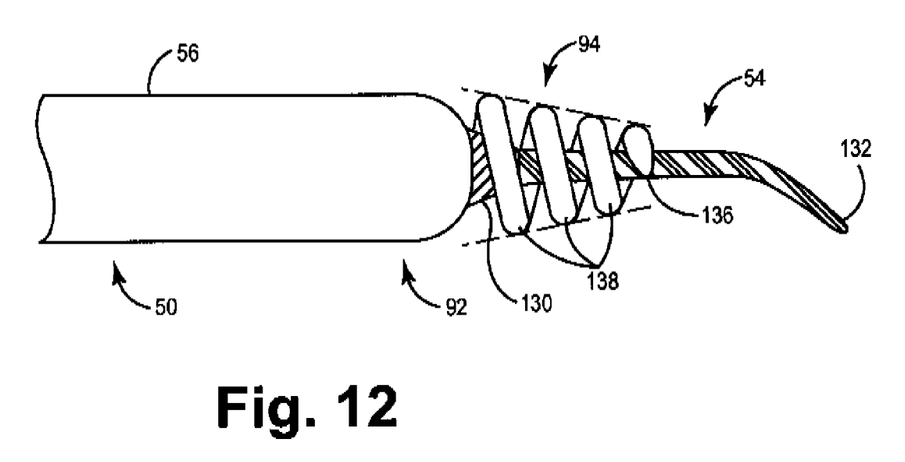
FIG. 12 is a plan view of a lead distal end according to one embodiment of the invention.

FIG. 12 is a plan view of a lead distal end according to one embodiment of the invention. Lead 50 may be embodied as unipolar, bipolar, or multipolar lead carrying one or more electrodes and/or other sensors with corresponding conductors extending through lead body 56 to a proximal lead connector assembly at proximal lead end 96 (shown in FIG. 11). Lead 50 includes distal fixation member 94 at distal lead end 92. Distal fixation member 94 is provided as an electrode that may be used for cardiac sensing and stimulation. As such, fixation member 94 is coupled to a conductor extending through lead body 56 to proximal connector pin 52 (shown in FIG. 11). In some embodiments, distal fixation member 94 may serve to fix distal lead end 92 at an implant site without functioning as an electrode. In alternative embodiments, lead 50 may carry additional electrodes and/or sensors, each coupled to corresponding conductors extending to respective connectors included in a proximal lead connector assembly.

Distal fixation member 94 is provided as a helix having a sharpened distal tip 136 for penetrating tissue at a targeted implant site. Upon rotation of lead 50 using advancement tool 30, helical fixation member 94 is rotated and advanced into a targeted tissue site, thereby fixating distal lead end 92 at the implant site. Fixation member 94 is provided with a generally conical shape having a narrower outer diameter near distal tip 136 and a wider outer diameter near distal lead end 92. The helical windings forming fixation member 94 may be provided with a convex leading edge 138 to form a smooth, atraumatic, conical outer contour of fixation member 94 for preventing damage to vein walls as distal lead end 92 is advanced forward in a cardiac vein to an implant site.

A guidewire guide 130 is provided extending from distal lead end 92, extending through one or more proximal windings of helical fixation member 94. Guidewire guide 130 directs guidewire 54 along the central axis of helical fixation member 94 as guidewire 54 is advanced past fixation member distal tip 136. The inner diameter of the distal windings of helical fixation member 94 closely conform to the outer surface of guidewire 54 such that fixation member 94 tracks closely along guidewire 54.

Figure 13:
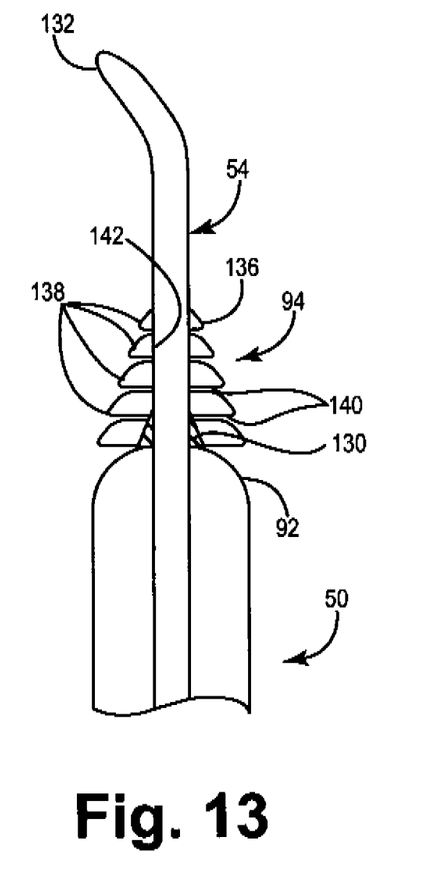
FIG. 13 is a sectional view of a conically shaped, helically wound fixation member according to one embodiment of the invention.

FIG. 13 is a sectional view of a conically shaped, helically wound fixation member according to one embodiment of the invention. The inner diameter 142 of fixation member 94 is shown to be substantially constant moving from the distal lead body end 92 to the sharpened tip 136 of fixation member 94. A wire used to from fixation member 94 would be provided with tapering outer dimensions such that, when wound to form the conically-shaped helix, the distal-most windings, near sharpened tip 136, have a smaller cross-sectional area than the proximal-most windings, near distal lead body end 92. The wire would be provided with a rounded or convex geometry along the surface that becomes the leading edge 138 of fixation member 94 as member 94 is advanced. The wire may be provided with a relatively flat geometry on the surface that becomes the proximal-facing surface 140 of helical fixation member 94. During lead retraction, the catheter would be moved forward very close to or over fixation member 94 to protect the surrounding tissue from the fixation member 94 as counterrotation is applied to retract the lead.

Thus, a transvenous lead and associated delivery system have been presented in the foregoing description with reference to specific embodiments. It is appreciated that various modifications to the referenced embodiments may be made without departing from the scope of the invention as set forth in the following claims. For example, it is recognized that the system may be used, with or without modifications, for providing a medical electrical lead implanted at other body locations, including endocardial locations, and is not limited to cardiac vein applications.

The invention claimed is:

1. A medical electrical lead system, comprising:
a catheter extending from a proximal catheter end to a distal catheter end;
a lead, insertable within the catheter, including a lead body extending from a proximal lead end to a distal lead end and an active fixation member positioned at the distal lead end;
an advancement tool for advancing the active fixation member outward from the distal catheter end, the advancement tool being adapted to be positioned around the lead body and further adapted to be removably fixedly engaged with the proximal catheter end.

2. The system of claim 1, wherein the catheter comprises a flexible distal portion proximate the distal end.

3. The system of claim 1, wherein the catheter forms an opening at the distal catheter end and a bend proximate the distal catheter end directing the opening away from a central axis of the catheter.

4. The system of claim 1, wherein the advancement tool includes a fixable member adapted to be removably fixedly engaged with the proximal catheter end and a movable member adapted to move laterally with respect to the fixable member and further adapted to be removably fixedly engaged with the lead body.

5. The system of claim 4, wherein the movable member is adapted to move laterally with respect to the fixable member upon rotation of the movable member.

6. The system of claim 4, wherein the movable member includes a fixation member for removably fixedly engaging the lead body.

7. The system of claim 1, further including a torque transfer member adapted to be interlockingly engaged with the advancement tool and removably fixedly engaged with the lead.

8. The system of claim 7, wherein the lead includes a lumen and the torque transfer member includes a stylet insertable within the lead lumen.

9. The system of claim 7, wherein the torque transfer member includes a fixation member for removably fixedly engaging the lead.

10. The system of claim 7, wherein the torque transfer member includes a receptacle for receiving and retaining the proximal lead end.

11. The system of claim 7 wherein the torque transfer member includes a first interlocking member and the advancement tool includes a second interlocking member adapted to interlockingly engage the first interlocking member.

12. The system of claim 1, wherein the catheter further includes a fluid injection port.

13. The system of claim 1, wherein the active fixation member includes a conically shaped helix.

14. The system of claim 13, wherein the active fixation member includes convex leading edges.

15. The system of claim 13, wherein the active fixation member includes a substantially constant inner diameter.

* * * * *